(12) United States Patent
Keller

(10) Patent No.: US 6,932,243 B2
(45) Date of Patent: Aug. 23, 2005

(54) DISPENSING ASSEMBLY WITH DYNAMIC MIXER

(75) Inventor: Wilhelm A. Keller, Merlischachen (CH)

(73) Assignee: Mixpac Systems AG, Rotkreuz (CH)

( * ) Notice: Subject to any disclaimer, the term of this patent is extended or adjusted under 35 U.S.C. 154(b) by 0 days.

(21) Appl. No.: 10/190,556

(22) Filed: Jul. 9, 2002

(65) Prior Publication Data

US 2002/0175186 A1 Nov. 28, 2002

Related U.S. Application Data

(63) Continuation of application No. 09/716,323, filed on Nov. 21, 2000, now Pat. No. 6,443,612.

(30) Foreign Application Priority Data

Dec. 2, 1999 (CH) .............................................. 2210/99
May 18, 2000 (EP) ............................................ 00810432

(51) Int. Cl.⁷ .............................................. B67D 5/56
(52) U.S. Cl. ................................. 222/145.6; 366/172.1
(58) Field of Search .......................... 366/172.1, 172.2, 366/176.1, 181.5, 307, 316, 328.2, 328.3, 329.2, 329.1; 222/145.5, 145.6

(56) References Cited

U.S. PATENT DOCUMENTS

| | | | | |
|---|---|---|---|---|
| 3,051,455 A | * | 8/1962 | Magester ................. | 366/172.1 |
| 3,226,093 A | * | 12/1965 | Gugel et al. ............... | 366/290 |
| 3,302,832 A | * | 2/1967 | Hardman et al. ............. | 222/94 |
| 3,390,814 A | * | 7/1968 | Creighton, Jr. et al. ..... | 222/137 |
| 3,570,719 A | * | 3/1971 | Schiff ......................... | 222/137 |
| 3,587,982 A | * | 6/1971 | Campbell ................... | 241/62 |
| 3,767,085 A | * | 10/1973 | Cannon et al. .............. | 222/82 |
| 4,107,793 A | * | 8/1978 | Wallace ...................... | 366/312 |
| 4,432,469 A | * | 2/1984 | Eble et al. .................. | 222/134 |
| 4,471,888 A | * | 9/1984 | Herb et al. .................. | 222/137 |
| 4,767,025 A | * | 8/1988 | Gebauer et al. ............. | 222/135 |
| 4,934,827 A | * | 6/1990 | Taschke et al. .......... | 366/162.3 |
| 4,951,843 A | * | 8/1990 | Paetow ..................... | 222/145.6 |
| 4,981,241 A | | 1/1991 | Keller | |
| 4,986,443 A | | 1/1991 | Saur et al. | |
| 5,249,709 A | | 10/1993 | Duckworth et al. | |
| 5,249,862 A | * | 10/1993 | Herold et al. ............... | 366/312 |
| 5,263,614 A | | 11/1993 | Jacobsen et al. | |
| 5,286,105 A | | 2/1994 | Herold et al. | |
| 5,400,925 A | | 3/1995 | Simmen | |
| 5,411,180 A | | 5/1995 | Dumelle | |
| 6,129,244 A | | 10/2000 | Horth | |
| 6,135,631 A | * | 10/2000 | Keller ......................... | 366/339 |
| 6,161,730 A | * | 12/2000 | Heusser et al. ............. | 222/137 |
| 6,168,052 B1 | | 1/2001 | Keller | |

(Continued)

FOREIGN PATENT DOCUMENTS

DE 3233366 * 9/1983
DE 33 07 558 A1 9/1984

(Continued)

*Primary Examiner*—Charles E. Cooley
(74) *Attorney, Agent, or Firm*—Foley & Lardner LLP

(57) ABSTRACT

A dynamic mixer configured to a double cartridge or a dispensing appliance, wherein the mixer includes two similarly configured inlets that are configured to connect to respective outlets of the double cartridge or the dispensing appliance, the outlets having either equal diameters wherein the inlets are inserted into the outlets of equal diameters, or the outlets have different diameters wherein one of the inlets fits over a smaller one of the outlets while another of the inlets fits into a larger one of the outlets. In another embodiment of the present invention, there is a dynamic mixer assembly including a dynamic mixer as just described, further attached to a double cartridge or a dispensing appliance.

9 Claims, 7 Drawing Sheets

U.S. PATENT DOCUMENTS

| | | | |
|---|---|---|---|
| 6,186,363 B1 * | 2/2001 | Keller et al. ............. | 222/145.6 |
| 6,244,740 B1 * | 6/2001 | Wagner et al. ........... | 366/181.5 |
| 6,290,101 B1 | 9/2001 | Chang | |
| 6,311,871 B1 * | 11/2001 | Binder .................... | 222/145.6 |
| 6,371,336 B1 * | 4/2002 | Keller | |
| 6,394,643 B1 * | 5/2002 | Bublewitz et al. ....... | 366/172.1 |
| 6,443,612 B1 * | 9/2002 | Keller ....................... | 366/307 |
| 6,457,609 B1 * | 10/2002 | Keller ....................... | 222/137 |
| 6,523,992 B1 * | 2/2003 | Bublewitz et al. ....... | 366/172.1 |
| 6,530,685 B1 * | 3/2003 | Mühlbauer et al. ........ | 366/336 |
| 6,540,395 B2 * | 4/2003 | Mühlbauer et al. ......... | 366/307 |
| 2002/0190082 A1 | 8/2002 | Keller | |
| 2003/0123323 A1 * | 7/2003 | Bublewitz et al. ....... | 366/172.1 |
| 2003/0137898 A1 * | 7/2003 | Wagner et al. ........... | 366/172.1 |

FOREIGN PATENT DOCUMENTS

| | | | |
|---|---|---|---|
| DE | 4235736 | * | 3/1994 |
| DE | 29705741 | * | 8/1998 |
| EP | 87029 | * | 8/1983 |
| EP | 0 057 465 B1 | | 9/1984 |
| EP | 0 492 412 B1 | | 12/1991 |
| EP | 0 492 413 B1 | | 11/1994 |
| EP | 0 956 908 A1 | | 11/1999 |
| EP | 1110599 | * | 6/2001 |
| EP | 1149627 | * | 10/2001 |
| WO | 98/43727 | * | 10/1998 |
| WO | 00/21652 | * | 4/2000 |
| WO | 01/24919 | * | 4/2001 |
| WO | 02/074426 | * | 9/2002 |

* cited by examiner

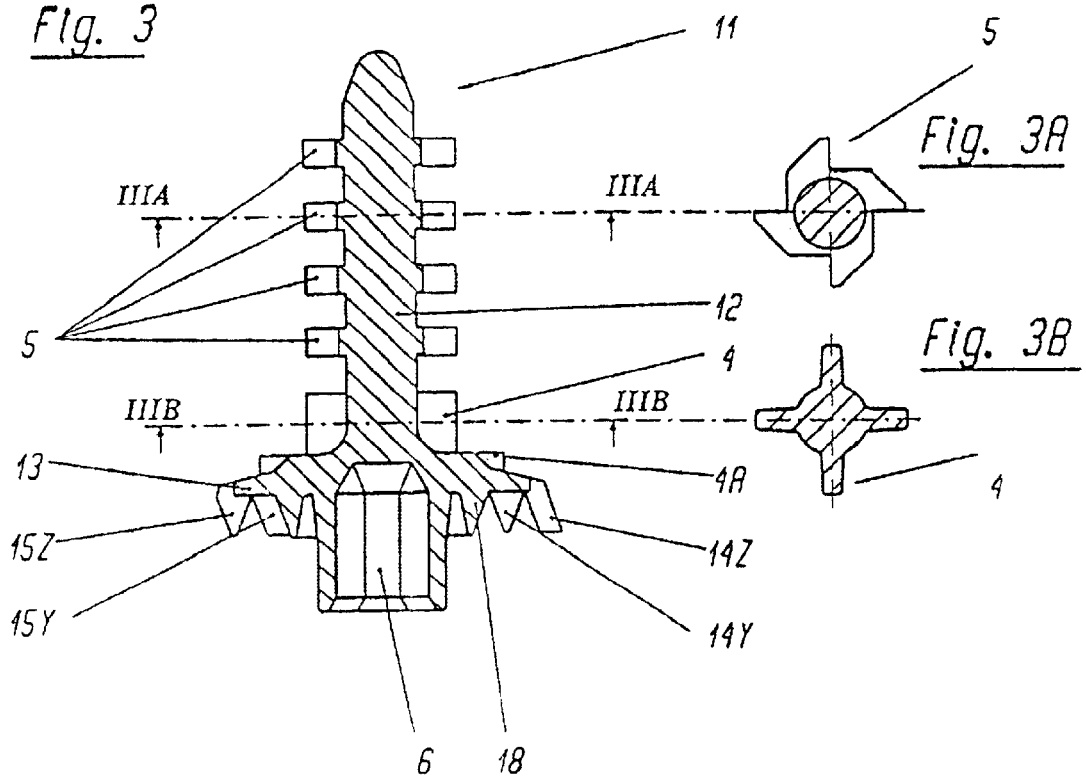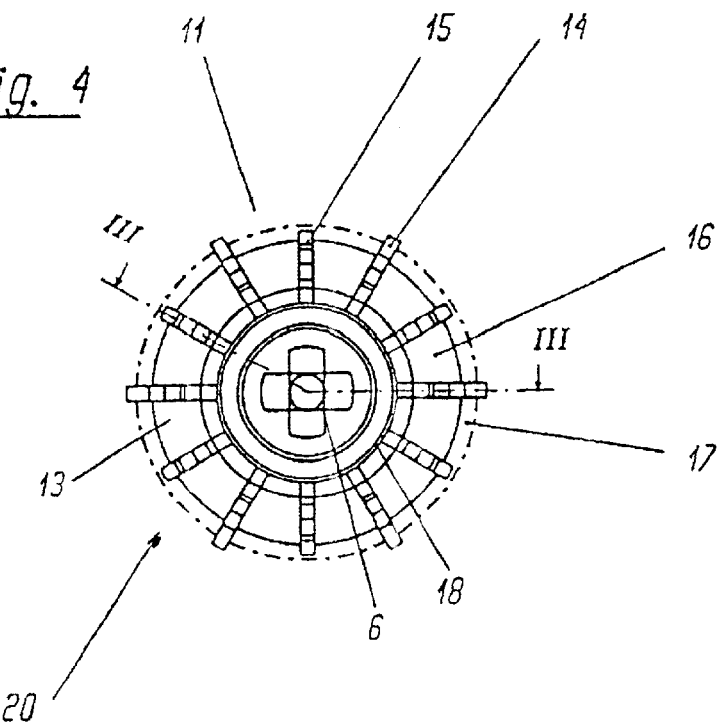

DISPENSING ASSEMBLY WITH DYNAMIC MIXER

This is a Continuation Application of U.S. patent application Ser. No. 09/716,323, now U.S. Pat. No. 6,443,612 B1, filed on Nov. 21, 2000, which claims priority from Switzerland Application Number 1999 2210/99, filed on Dec. 02, 1999 and from European Application Number 00810432.5 filed on May 18, 2000. The disclosures of the just mentioned applications and/or patents are incorporated by reference herein in their entirety.

FIELD OF THE INVENTION

The present invention refers to a dynamic mixer comprising a rotor housing in which a rotatable mixing rotor is arranged, said rotor housing being closed by a plate-shaped cover on the inlet side which is provided with inlets for the components to be mixed.

BACKGROUND OF THE INVENTION

A mixer of this kind is known from European Patent Application No. 0,492,412. An essential feature of this mixer is a plate-shaped connecting member comprising a wiper of a particular design on the mixing rotor.

SUMMARY OF THE INVENTION

On the background of this prior art, it is the object of the present invention to provide a dynamic mixer allowing to achieve an improved mixing quality as well as an increased mixing performance. This object is attained by a dynamic mixer wherein the mixing rotor comprises a rotor disk for the purpose of premixing said components, which is disposed near the inlets and whose surface is provided on the inlet side with means for carrying along the components to be mixed, said rotor disk comprising gaps allowing the passage of said components to the back side of said rotor disk and to the rotor hub, which are provided with mixing elements.

Preferred embodiments of the invention are defined in the dependent claims.

BRIEF DESCRIPTION OF THE DRAWINGS

The invention will be explained in more detail hereinafter with reference to drawings of exemplary embodiments, where

FIG. 3 shows a cross-section of a second embodiment of a mixing rotor of the invention according to line III—III in FIG. 4;

FIG. 3A shows a cross-section according to line IIIA—IIIA in FIG. 3;

FIG. 3B shows a cross-section according to line IIIB—IIIB in FIG. 3;

FIG. 4 shows the mixing rotor of FIG. 3 as seen from the inlet side;

DETAILED DESCRIPTION OF THE INVENTION

Figure 1:
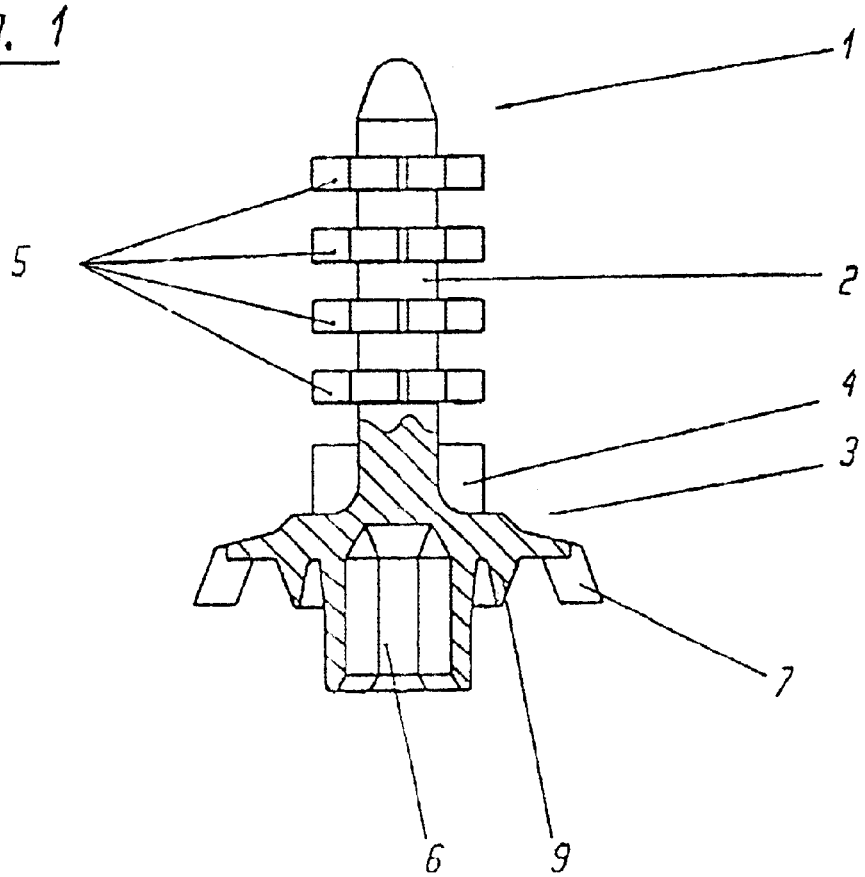
FIG. 1 shows a side elevation and partial section of a first embodiment of a mixing rotor of the invention.
Figure 2:
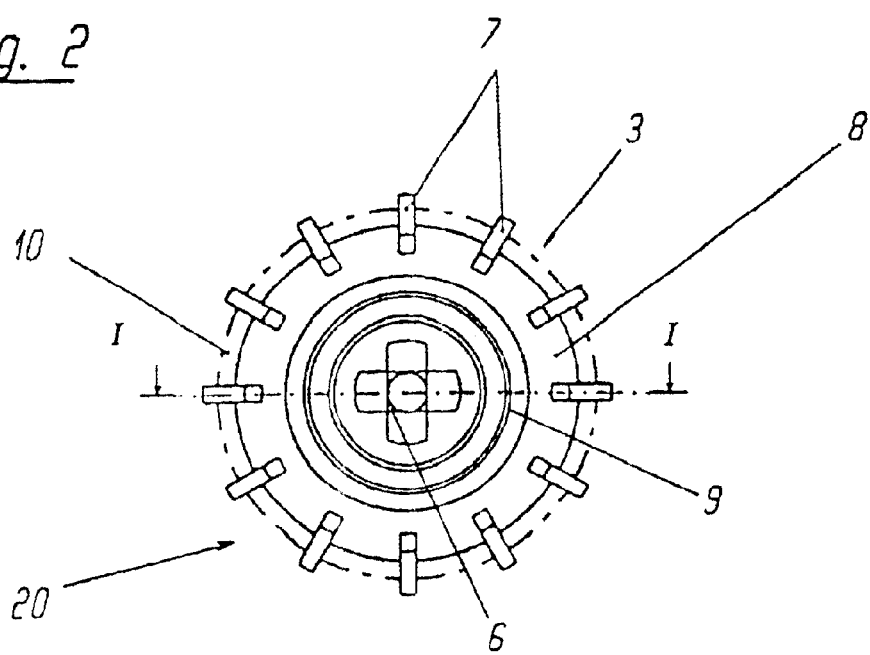
FIG. 2 shows the mixing rotor of FIG. 1 as seen from the inlet side.
Figure 5:
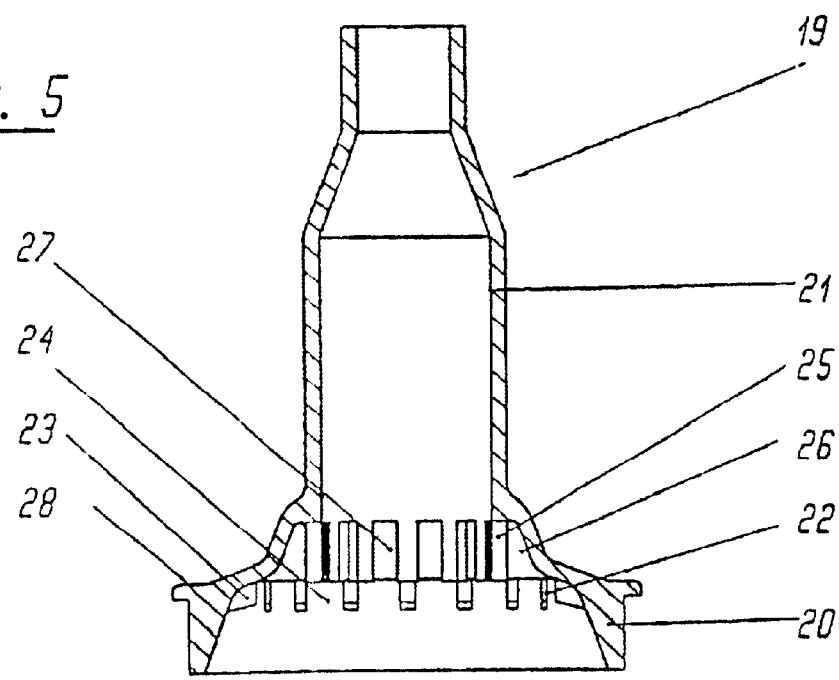
FIG. 5 shows the rotor housing of a mixer of the invention according to cross-section V—V in FIG. 6.
Figure 6:
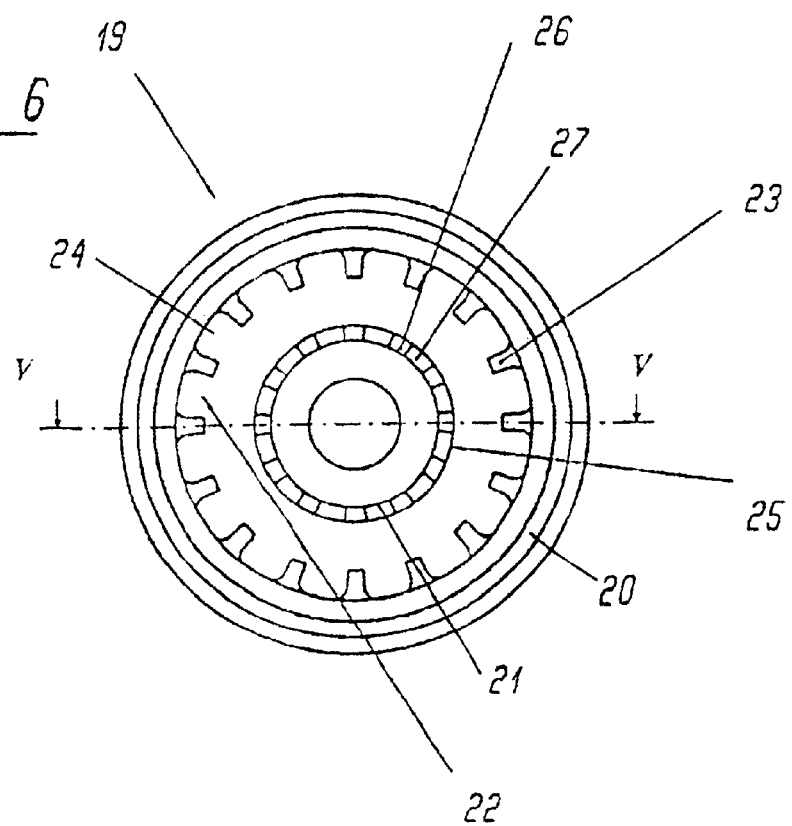
FIG. 6 shows the rotor housing of FIG. 5 as seen from the inlet side.

The dynamic mixer of the invention is composed of a mixing rotor and a rotor housing comprising a rotor housing cover. FIGS. 1 and 2 illustrate a first embodiment of a mixing rotor, and FIGS. 3 and 4 show a second one.

Mixing rotor 1 of FIGS. 1 and 2 essentially consists of a rotor hub 2 comprising a rotor disk 3 on the inlet side. The back side of the rotor disk is provided with mixing blades 4 which are followed by mixing projections 5. According to FIGS. 2 and 4, on the inlet side, the rotor hub comprises a driver opening 6 for engagement with the driver of the mixer driving shaft which may have various shapes, e.g. rectangular, hexagonal, or cross-recessed.

On the inlet side, the rotor disk is provided with chamber partitions 7 which divide the rotor disk into chamber sections 8. These sections serve for the metered, alternating and diametrically offset intake of the two components to be mixed and for their further transport. In order to prevent a stemming of the components, partitions 7 are shortened, i.e. they are not thoroughgoing. The rotor disk further comprises a collar 9 intended to cooperate with a sealing lip 34 attached to the rotor housing. Between the rotor housing and the circumference of the rotor disk, annular gaps 10 are created which are interrupted by partitions 7 and through which the components pass to the back side of the rotor disk and from there to the mixing elements in the cylindrical portion of the housing.

With reference to the second embodiment of a mixing rotor according to FIGS. 3 and 4, mixing rotor 11 with rotor hub 12 is provided with a rotor disk 13 on the inlet side. Mixing blades 4 as well as additional mixing blades 4A are disposed on the back side of the rotor disk and followed by mixing projections 5. FIG. 3A shows the cross-section of mixing projections 5 and FIG. 3B that of mixing blades 4.

On the inlet side, rotor disk 13 is provided with carriers of alternating outward extension, i.e. carriers 15 project less to the periphery than carriers 14. Carriers 14 and 15 have a tooth-shaped profile, and respective blades 15Y or 15Z provided on carrier 15 are staggered with respect to blades 14Y or 14Z on carrier 14.

In this manner, the inlet side of the rotor disk is divided into partly open chamber sections 16 which serve for the metered, diametrically offset and alternating intake and for the further transport of the two components to be mixed, thus contributing to premixing. In this embodiment as well, the components coming from the inlets can only pass to the back side of the rotor disk through the annular gaps between the circumference of the rotor disk and the rotor housing. However, it is also possible to provide annular gaps which are closer to the center, either combined with the peripheral gaps or exclusively. Furthermore, the rotor disk comprises a collar 18 intended to cooperate with the above-mentioned sealing lip.

Mixing rotor 1 or 11 is disposed in a bipartite rotor housing as illustrated in FIGS. 5 to 8. Rotor housing 19 according to FIGS. 5 and 6 comprises a plate-shaped housing portion 20 receiving rotor disk 13 and a cylindrical housing portion 21 receiving rotor hub 12. The bottom surface of plate-shaped housing portion 20 comprises a first, outer stator comb composed of individual ridges 23, the premixed components passing through the spaces 24 between the ridges to the second, inner stator comb 25 comprising inner ridges 26 with spaces 27 through which the premixed components pass to mixing blades 4A, 4 and to mixing projections 5 in order to be divided and mixed once again. The plate-shaped housing portion further comprises a contact surface 28 for a bayonet ring 35.

Figure 7:
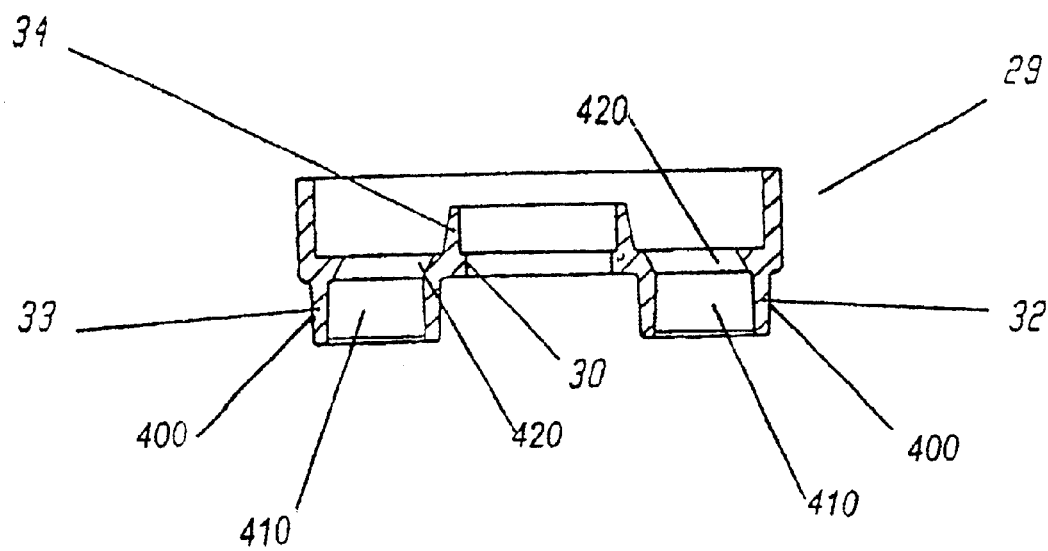
FIG. 7 shows the cover of the rotor housing of FIGS. 5 and 6 according to section VII—VII in FIG. 8.
Figure 8:
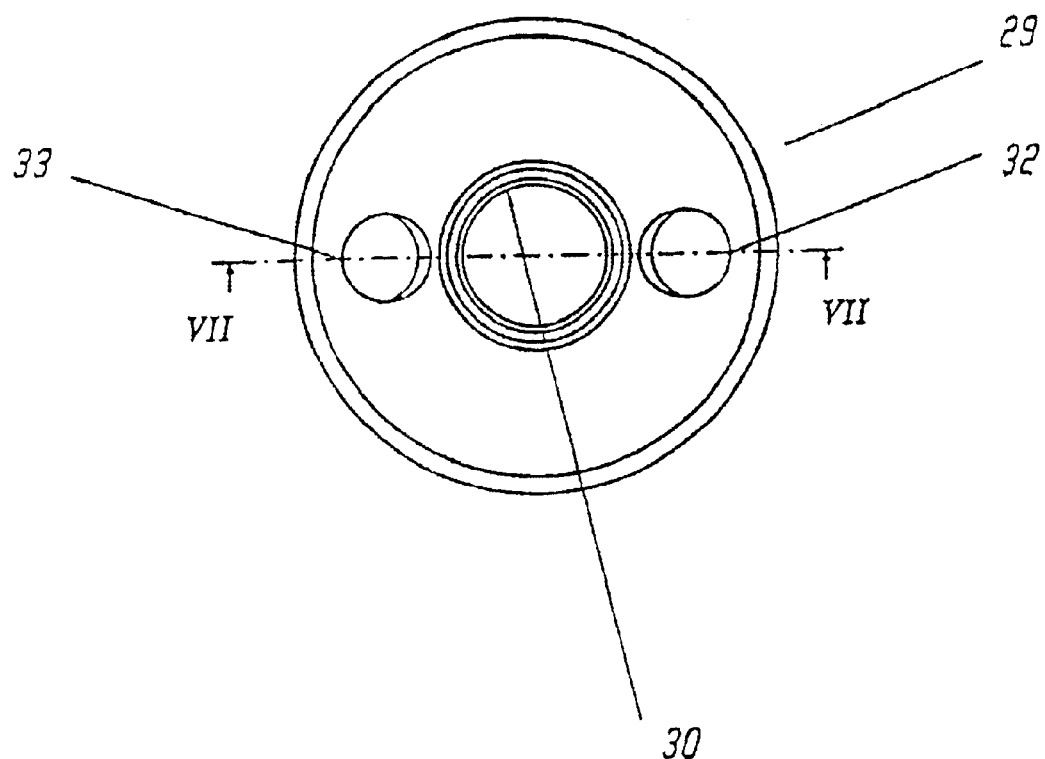
FIG. 8 shows the rotor housing cover as seen from the outlet side.

FIGS. 7 and 8 show a rotor housing cover 29 comprising a rotor bearing 30 receiving the carrier hub 31 and two similar inlets 32 and 33. For a good sealing of the carrier hub, rotor housing cover 29 is provided with a sealing lip 34. 13. As can be seen from FIGS. 7 and 8, in an embodiment of the present invention, each of the two inlets 32, 33 comprises a cylindrical projection 400 having a first hollow portion 410, the cylindrical projections 400 being attached to or formed into the cover 29 of the dynamic mixer. Still further, as can be seen from FIGS. 7 and 8, the cover may include second hollow portions 420 which are proximate to the first hollow portions 410, the second hollow portions being angled with respect to the first hollow portions. Additionally, as can be seen from these figures, the hollow portions are configured to channel components to be mixed into the dynamic mixer, and the cross sections normal to the direction of channeling of the first hollow portions are substantially similar to the cross sections normal to the direction of channeling of the second hollow portions. FIGS. 7–10 show that the area of the cross sections normal to the direction of channeling of the second hollow portions may be substantially equal to each other.

It is also possible to provide further stator elements on cylindrical housing portion 21 in the area of the crowns of mixing projections in order to obtain a further improved mixing quality.

Figure 9:
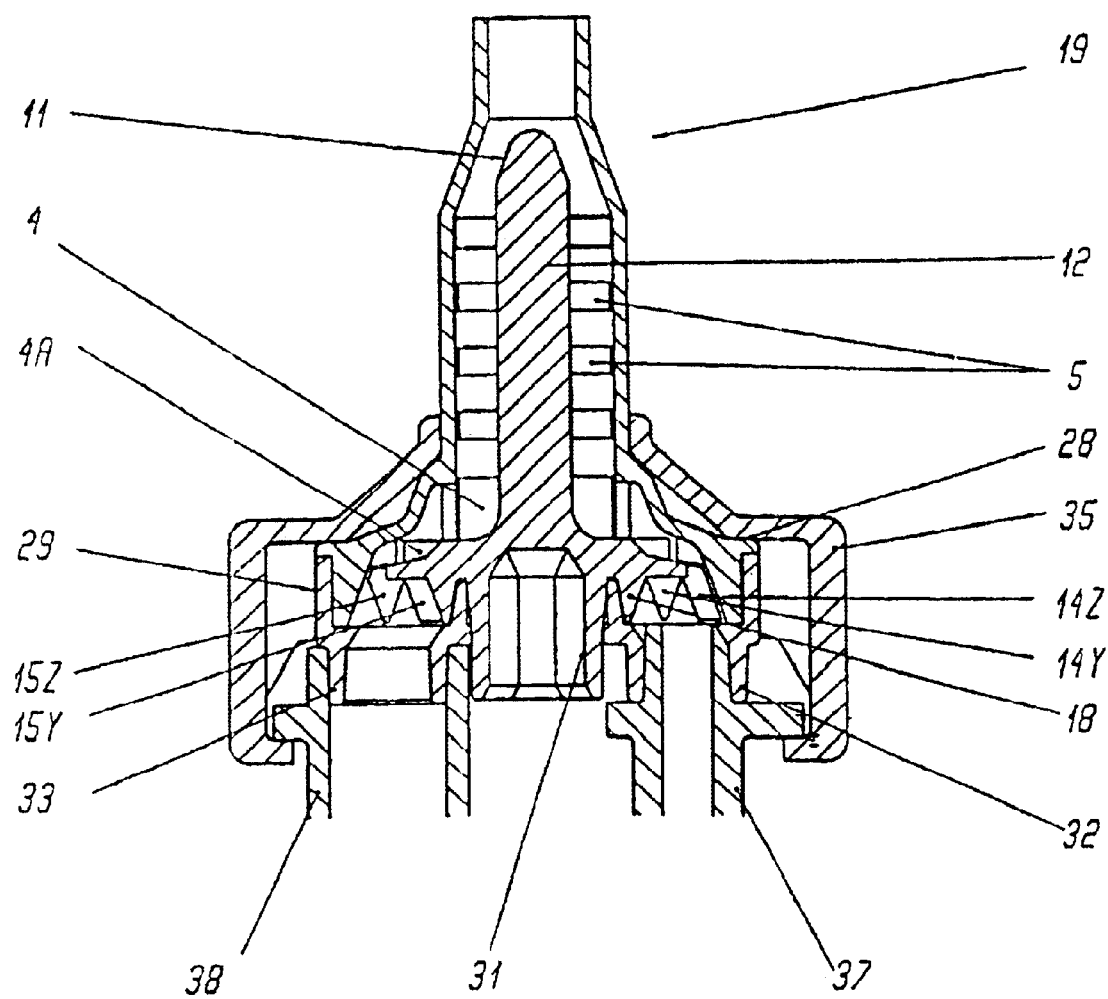
FIG. 9 shows a longitudinal section of the assembled mixer of FIGS. 3 to 8 connected to outlets of different diameters.
Figure 10:
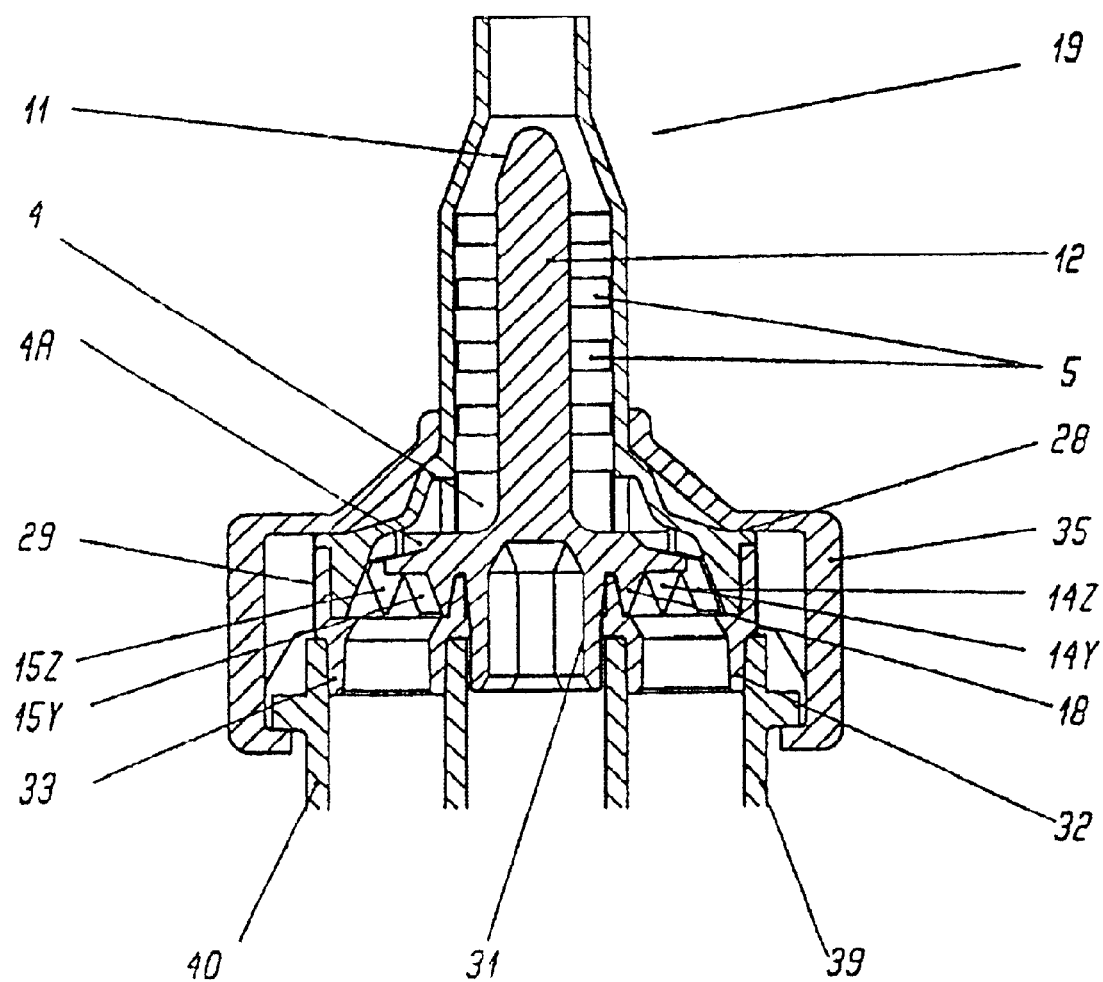
FIG. 10 shows a longitudinal section of the assembled mixer of FIGS. 3 to 8 connected to outlets of equal diameters.

FIGS. 9 and 10 illustrate that a suitably dimensioned mixer of the invention can be used both for double cartridges or dispensing appliances having outlets of equal diameters and for double cartridges or dispensing appliances having outlets of different diameters, even regardless of its orientation.

FIG. 9 shows a cross-section of an assembled mixer having equally dimensioned inlets, the mixer being connectable to a double cartridge or a dispensing appliance having containers of a cross-sectional ratio of 5:1 and outlets of different diameters. In FIG. 9, only outlets 37 and 38 are illustrated. One inlet 32 of the mixer fits over smaller outlet 37, and the other inlet 33 of the mixer fits into larger outlet 38, the mixer being attachable without a previous orientation.

FIG. 10 illustrates that the same mixer as in FIG. 9 is also connectable to a double cartridge or a dispensing appliance having equal outlets, the two inlets 32, 33 of the mixer being insertable into outlets 39, 40, again requiring no previous orientation.

The just described configurations of the inlets and outlets are particularly advantageous for a dynamic mixer. Specifically, the configurations allows the components to be mixed to form component streams which have the effect of enhancing the dynamic mixing effect. This is readily seen in the case of a double cartridge or a dispensing appliance having outlets of different diameters. When one of the inlets of the mixer is inside the larger outlet, as is seen in FIG. 9, the component stream is smaller and nearer in size to the material stream of the smaller outlet, thus providing better mixing results over a stream from a large outlet and a stream from a small outlet, where the size of the stream is determined solely by the size of the outlet.

Figure 11:
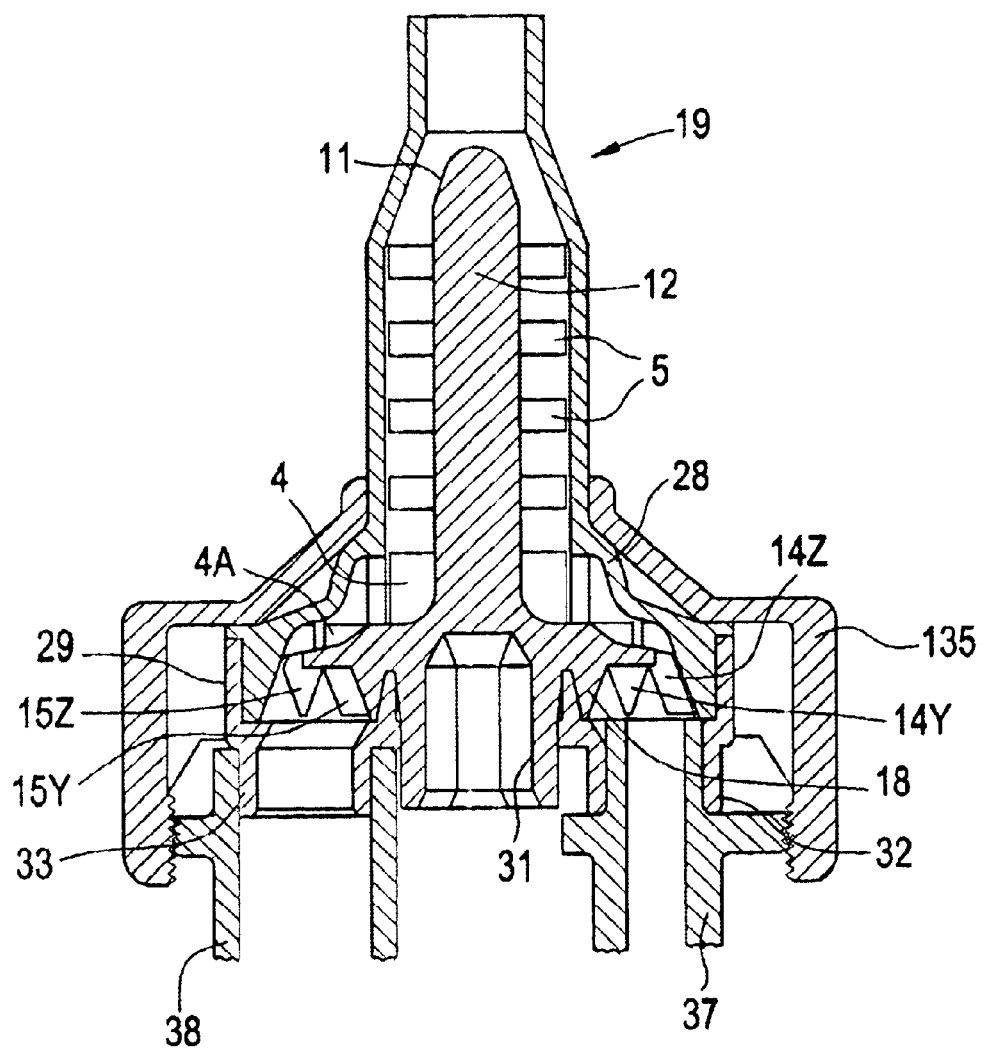
FIG. 11 shows the dynamic mixer attached to an outlet end of a double cartridge or dispensing appliance with a screw nut.

In both embodiments, the mixer is secured by means of a bayonet ring 35 or alternatively an internally threaded screw nut 135, as may be seen in FIG. 11. The same mixer can also be used for double cartridges or dispensing appliances having cross-sectional and outlet diameter ratios other than 1:1 and 5:1, e.g. 10:1.

As compared to known dynamic mixers of the same construction length, the described arrangement allows a substantially increased mixing power and quality at lower speeds and operates with a relatively low back pressure. The invention is not limited to the illustrated shapes but different shapes of the chamber sections and of the stator combs, mixing ridges, or mixing projections are possible within the scope of the invention.

What is claimed:

1. A dispensing assembly comprising:
   a dynamic mixer including at least one rotor and at least two similarly configured inlets; and
   a double cartridge or a dispensing appliance, wherein the double cartridge or dispensing appliance includes outlets of different configuration, and wherein one inlet fits over one outlet of different configuration and one inlet fits into one outlet of different configuration.

2. The dynamic mixer of claim 1, wherein each of the two inlets comprises a cylindrical projection having a first hollow portion.

3. The dynamic mixer of claim 2, wherein the cylindrical projections are attached to or formed into a cover of the dynamic mixer.

4. The dynamic mixer of claim 2, wherein the mixer further includes second hollow portions which are proximate to the first hollow portions, the second hollow portions being angled with respect to the first hollow portions.

5. The dynamic mixer of claim 4, wherein the hollow portions are configured to channel components to be mixed into the dynamic mixer, and wherein cross sections normal to the direction of channeling of the first hollow portions are substantially similar to the cross sections normal to the direction of channeling of the second hollow portions.

6. The dynamic mixer of claim 4, wherein the hollow portions are provided to channel components to be mixed into the dynamic mixer, and wherein the area of the cross sections normal to the direction of channeling of the second hollow portions are substantially equal to each other.

7. The dynamic mixer of claim 1, wherein the dynamic mixer is adapted to attach to an outlet end of the double cartridge or to a dispensing appliance with a bayonet ring.

8. The dynamic mixer of claim 1, wherein the dynamic mixer is adapted to attach to an outlet end of the double cartridge or to a dispensing appliance with a screw nut.

9. A dispensing assembly according to claim 1, wherein the two similarly configured inlets are adapted to also connect to respective outlets of another double cartridge or dispensing appliance having equal diameters, wherein the inlets are inserted into said outlets of equal diameters.

* * * * *